US00PP10453P

United States Patent [19]

Tanaka et al.

[11] Patent Number: Plant 10,453

[45] Date of Patent: Jun. 16, 1998

[54] FUCHSIA PLANT—'SANICOMF'

[75] Inventors: Toshi Tanaka, Ashiya; Hidefumi Funakoshi, Takarazuka; Kenkichi Nose, Ashiya; Ushio Sakazaki, Hikone, all of Japan

[73] Assignees: Nishinomiya City, Hyogo; Suntory Limited, Osaka, both of Japan

[21] Appl. No.: 788,462

[22] Filed: Jan. 28, 1997

[51] Int. Cl.[6] ..... A01H 5/00

[52] U.S. Cl. ..... Plt./84

[58] Field of Search ..... Plt./84

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

Disclosed herein is a fuchsia plant, having a spreading growth habit of strongly bushy form, low plant height, fine branching, and short internode length. The plant shape is compact. The fuchsia plant has great profusion blooms, the whole bush remaining in bloom for a considerable period of time, and very long flowering duration. The flowers are single and do not have variegated patterns on the petals, the petals are deep violet in color having a deep purplish pink calyx tube also without any variegated pattern. The plant has a high resistance to heat, cold, disease and pests, and is able to grow in an outdoor garden during the term of intense summer heat.

2 Drawing Sheets

BACKGROUND OF THE VARIETY

The present invention relates to a new and distinct variety of fuchsia plant obtained from the crossing of one fuchsia plant "FR20" (♂) native to Brazil and the other fuchsia plant "Fuchsia hybrida 1" (♀).

The fuchsia plant is a very popular plant in the United States and Europe and is used for potting in the spring season to summer season. But, the fuchsia plants have a weak resistance to heat and it is necessary to grow them in air-conditioned rooms, especially in the Japanese summer where the heat is intense. For this reason fuchsia plants became unpopular. Accordingly, this invention was aimed at obtaining a new variety having a strong resistance to heat and spreading growth habit with fine branching.

The new variety of fuchsia plant according to this invention originated from crossing one fuchsia plant called "FR20" (♂) native to Brazil and the other fuchsia plant "Fuchsia hybrida 1" (♀).

First of all, one wild type of fuchsia plant called "FR20" was selected from 190 fuchsia plant varieties native to Brazil in which the seeds were introduced to Japan in February, 1991. And then 500 seedlings were obtained from crossing the wild type of fuchsia plant called "FR20" native to Brazil as pollen parent and the other fuchsia plant "Fuchsia hybrida 1" as female parent in the spring, 1992. From this crossing, 119 seedlings were selected in view of heat resistance and growth habit and then 19 seedlings were selected for a heat residence test in an outdoor garden in 1993. These 19 seedlings were grown and carried out a trial by flower potting in an open-air field from the spring of 1994. The summer of 1994 had abnormal weather and was more intense than usual, and then one plant which could be grown in an open-air field exhibited excellent results from an apical meristem culture test. This plant was selected in the Autumn, 1994. The botanical characteristics of the finally-selected plant was examined and compared with similar varieties "Fuchsia hybrida 1" and "Fuchsia hybrida 2" from the spring of 1994. As a result, it was concluded that this fuchsia is distinguishable from any other variety, whose existence is known to us, sufficiently uniform and stable in its characteristics. This new variety of fuchsia plant was named "Sanicomf".

In the following description, the color-coding is in accordance with the Horticultural Color Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The pollen parent used in the crossing of "Sanicomf" was a wild type of fuchsia plant called "FR20" native to Brazil, the seeds were introduced to Japan in February, 1991. The fuchsia plant "FR20" has a spreading growth habit, brightly colored red sepal, single flowers, deep violet colored petal, and a high resistance to heat.

The female parent used in the crossing of "Sanicomf" was "Fuchsia hybrida 1". "Fuchsia hybrida 1" was a garden variety and was bought from a shop in the spring of 1992 in Hyogo-ken, Japan.

The wild type of fuchsia plants "FR20" and the garden variety "Fuchsia hybrida 1" are presently maintained at the Plant Biotechnology Laboratory of Suntory Ltd., residing at 863-1, Aza-Iketani, Oomoricho, Youkaichi-shi, Shiga-ken, Japan and at the Plant Research Center of Nishinomiya-shi, residing at 1-1, Kitayama-cho, Nishinomiya-shi, Hyogo-ken, Japan.

"Fuchsia hybrida 1" which is the female parent of "Sanicomf" used for examination as a comparison are as follows.

Plant:
- *Growth habit.*—Spreading.
- *Plant height.*—Medium.
- *Grade of bushiness.*—Medium.

Stem:
- *Thickness.*—2.4 mm.
- *Color.*—Red.
- *Pubescence.*—Normal.
- *Branching.*—Medium.
- *Length of internode.*—Medium.

Leaf:
- *Phyllotaxis.*—Opposite.
- *Shape.*—Ovate.
- *Tip form of leaf.*—Acute.

*Base form of leaf.*—Orbicular.
*Shape of Margin.*—Dentate serrate.
*Length.*—44.5 mm.
*Width.*—23.4 mm.
*Thickness.*—0.3 mm.
*Color of upper surface of new leaf.*—Dark olive green. (R.H.S. 139A, JHS 3707).
*Color of upper surface of mature leaf.*—Dark yellowish green. (R.H.S. 139A, JHS 4007).
*Color of under surface of mature leaf.*—Moderate yellow green (R.H.S. 146B, JHS 3514) with deep red (R.H.S. 60A, JHS 0108) dots.
*Variegation on upper surface.*—Absent.
*Color of leaf vein.*—Purplish red.
*Luster.*—Absent.
*Pubescence of upper surface.*—Few.
*Pubescence of under surface.*—Few.
*Length of petiole.*—17.0 mm.
*Width of petiole.*—15 mm.
*Color of petiole.*—Deep red. (R.H.S. 60A, JHS 0108).
*Pubescence of petiole.*—Medium.

Flower:
*Inflorescence types.*—Leaf axil—single.
*Facing direction.*—Downward to horizontal.
*Type.*—Single.
*Diameter.*—37.6 mm.
*Length.*—29.1 mm.
*Diameter of corolla.*—Medium.
*Shape of petal.*—Obovate.
*Length of petal.*—18.1 mm.
*Width of petal.*—17.9 mm.
*Thickness of petal.*—0.3 mm.
*Number of petals.*—Medium;4.
*Color of petal at the beginning of blooming time.*—Pinkish white. (R.H.S. 49C, JHS 0101).
*Color of petal at blooming time.*—Pinkish white. (R.H.S. 49C, JHS 0101).
*Variegated pattern of petal.*—Present; vein pattern.
*Color of variegated pattern of petal.*—Vivid red. (R.H.S. 57A, JHS 0107).
*Shape of sepal.*—Oblong.
*Tip form of sepal.*—Acute.
*Calyx rolling.*—Medium (half up).
*Intorsion of sepal.*—Medium.
*Curvature of sepal.*—Flat.
*Length of sepal.*—30.5 mm.
*Width of sepal.*—7.9 mm.
*Thickness of sepal.*—0.5 mm.
*Number of sepals.*—Medium; 4.
*Color of sepal.*—Deep pink. (R.H.S. 51A, JHS 0113).
*Variegated pattern on sepal.*—Present; vein pattern.
*Color of variegated pattern of sepal.*—Deep pink. (R.H.S. 51A, JHS 0113).
*Shape of calyx tube.*—Long-tubular.
*Thickness of calyx tube.*—4.4 mm.
*Length of calyx tube.*—9.0 mm.
*Color of calyx tube.*—Deep pink. (R.H.S. 51A, JHS 0113).
*Variegated pattern on calyx tube.*—Present; vein pattern.
*Color of variegated pattern of calyx tube.*—Vivid red. (R.H.S. 57A, JHS 0107).
*Length of pistil.*—Long.
*Color of pistil.*—Strong purplish pink. (R.H.S. 55A, JHS 9705).
*Color of stigma.*—Strong purplish pink. (R.H.S. 55A, JHS 9705).
*Length of stamen.*—Medium.
*Color of stamen.*—Strong purplish pink. (R.H.S. 55A, JHS 9705).
*Number of stamens.*—Medium; 8.
*Thickness of peduncle.*—Medium.
*Length of peduncle.*—Medium.
*Color of peduncle.*—Vivid yellow green. (R.H.S. 140A, JHS 3105).
*Shape of ovary.*—Elliptic.
*Length of ovary.*—Short.
*Color of ovary.*—Strong yellow green. (R.H.S. 143A, JHS 3711).
*Number of flowers.*—Medium.
*Flower fragrance.*—Absent.
*Floriferousness.*—Few.
*Grade of seed fertility.*—Medium.
*Grade of floral abscission.*—Easy.
*Blooming time.*—Early.
*Flowering duration.*—Short; May to June and September to October.

Physiological and ecological characteristics:
*Grade of cold resistance.*—Medium.
*Grade of heat resistance.*—Medium.
*Grade of disease resistance.*—Strong.
*Grade of pest resistance.*—Medium.

"Fuchsia hybrida 2" was used for examination as a comparison are as follows.

Plant:
*Growth habit.*—Spreading.
*Plant height.*—Medium.
*Grade of bushiness.*—Few.

Stem:
*Thickness.*—1.7 mm.
*Color.*—Purplish red.
*Pubescence.*—Few.
*Branching.*—Medium.
*Length of internode.*—Short.

Leaf:
*Phyllotaxis.*—Opposite.
*Shape.*—Elliptic.
*Tip form of leaf.*—Acute.
*Base form of leaf.*—Orbicular.
*Shape of margin.*—Dentate serrate.
*Length.*—38.6 mm.
*Width.*—24.4 mm.
*Thickness.*—0.3 mm.
*Color of upper surface of new leaf.*—Moderate olive green. (R.H.S. 146A, JHS 3508).
*Color of upper surface of mature leaf.*—Dark olive green. (R.H.S. 132A, JHS 3708).
*Color of under surface of mature leaf.*—Strong yellow green. (R.H.S. 143A, JHS 3711).
*Variegation on upper surface.*—Absent.
*Color of leaf vein.*—Pale green.
*Luster.*—Weak.
*Pubescence of upper surface.*—Few.
*Pubescence of under surface.*—Few.
*Length of petiole.*—15.4 mm.
*Width of petiole.*—1.4 mm.
*Color of petiole.*—Moderate red. (R.H.S. 184B, JHS 0115).
*Pubescence of petiole.*—Few.

Flower:

*Inflorescence types.*—Leaf axil—single.
*Facing direction.*—Downward to horizontal.
*Type.*—Double.
*Diameter.*—39.9 mm.
*Length.*—29.8 mm.
*Diameter of corolla.*—Medium.
*Shape of petal.*—Obovate.
*Length of petal.*—13.7 mm.
*Width of petal.*—13.5 mm.
*Thickness of petal.*—0.3 mm.
*Number of petals.*—Numerous; over 8.
*Color of petal at the beginning of blooming time.*—Deep purple. (R.H.S. 86A, JHS 8307).
*Color of petal at blooming time.*—Deep purple. (R.H.S. 86A, JHS 8307).
*Variegated pattern of petal.*—Present; primary pattern is splashed pattern, secondary pattern is vein pattern.
*Color of variegated pattern of petal.*—Color of primary pattern is purple, color of secondary pattern is red.
*Shape of sepal.*—Ovate.
*Tip form of sepal.*—Acuminate.
*Calyx rolling.*—None (full down).
*Intorsion of sepal.*—None.
*Curvature of sepal.*—Incurve.
*Length of sepal.*—18.3 mm.
*Width of sepal.*—11.2 mm.
*Thickness of sepal.*—0.5 mm.
*Number of sepals.*—Medium; 4.
*Color of sepal.*—Strong red.
*Variegated pattern on sepal.*—Absent.
*Shape of calyx tube.*—Long-tubular.
*Thickness of calyx tube.*—4.8 mm.
*Length of calyx tube.*—2.0 mm.
*Color of calyx tube.*—Strong purplish red. (R.H.S. 57D, JHS 9706).
*Variegated pattern on calyx tube.*—Absent.
*Length of pistil.*—Medium.
*Color of pistil.*—Vivid red. (R.H.S. 52A, JHS 0106).
*Color of stigma.*—Deep purplish pink. (R.H.S. 55A, JHS 9705).
*Length of stamen.*—Medium.
*Color of stamen.*—Vivid red. (R.H.S. 57A, JHS 0107).
*Number of stamens.*—Medium; 8.
*Thickness of peduncle.*—Medium.
*Length of peduncle.*—Medium.
*Color of peduncle.*—Moderate red. (R.H.S. 181B, JHS 0416).
*Shape of ovary.*—Oblong.
*Length of ovary.*—Medium.
*Color of ovary.*—Strong yellow green. (R.H.S. 144A, JHS 3507).
*Number of flowers.*—Few.
*Flower fragrance.*—Absent.
*Floriferousness.*—Medium.
*Grade of seed fertility.*—Low.
*Grade of floral abscission.*—Medium.
*Blooming time.*—Early.
*Flowering duration.*—Short; May to June and September to October.

Physiological and ecological characteristics:

*Grade of cold resistance.*—Medium.
*Grade of heat resistance.*—Medium.
*Grade of disease resistance.*—Strong.
*Grade of pest resistance.*—Medium.

This new and distinct variety of fuchsia plant, "Sanicomf", was asexually reproduced by cutting at the aforementioned at the Plant Biotechnology Laboratory of Suntory Ltd. and the Plant Research Center of Nishinomiya-shi, and the homogeneity and stability thereof were confirmed.

SUMMARY OF THE VARIETY

The new variety of fuchsia plant has a spreading growth habit with fine branching, short internode length, low plant height, strong bushy and verticillate leaf phyllotaxis which is very different from a similar variety, "Fuchsia hybrida 1"(♀) having spreading growth habit with medium branching, medium internode length, medium bushiness and opposite leaf phyllotaxis. The plant shape of this new variety is compact. The new variety of fuchsia plant has great profusion of blooms and very long flowering duration, deep violet colored flower petals without variegated pattern, deep purplish pink colored sepal without variegated pattern and deep purplish pink colored calyx tube without variegated pattern, which is clearly distinguished from "Fuchsia hybrida 1"(♀)" having pinkish white colored flower petals with purple vein pattern, deep pink colored sepal with vivid red vein pattern and deep pink colored calyx tube with vivid red vein pattern. The new variety of fuchsia plant has a high resistance to heat, cold, disease and pests, and is able to be grown in an outdoor garden during the term of intense summer heat.

DESCRIPTION OF THE VARIETY

Figure 1:
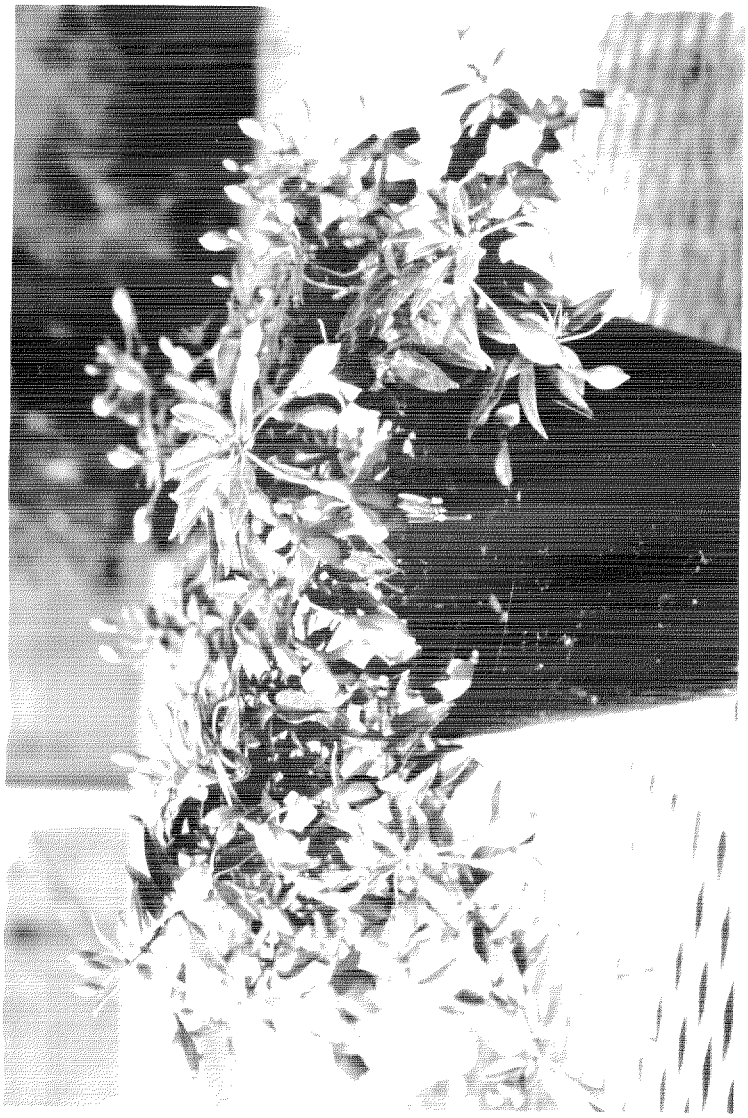
FIG. 1 is a photograph giving a partial view of the new variety of fuchsia plant planted in a flower pot.
Figure 2:
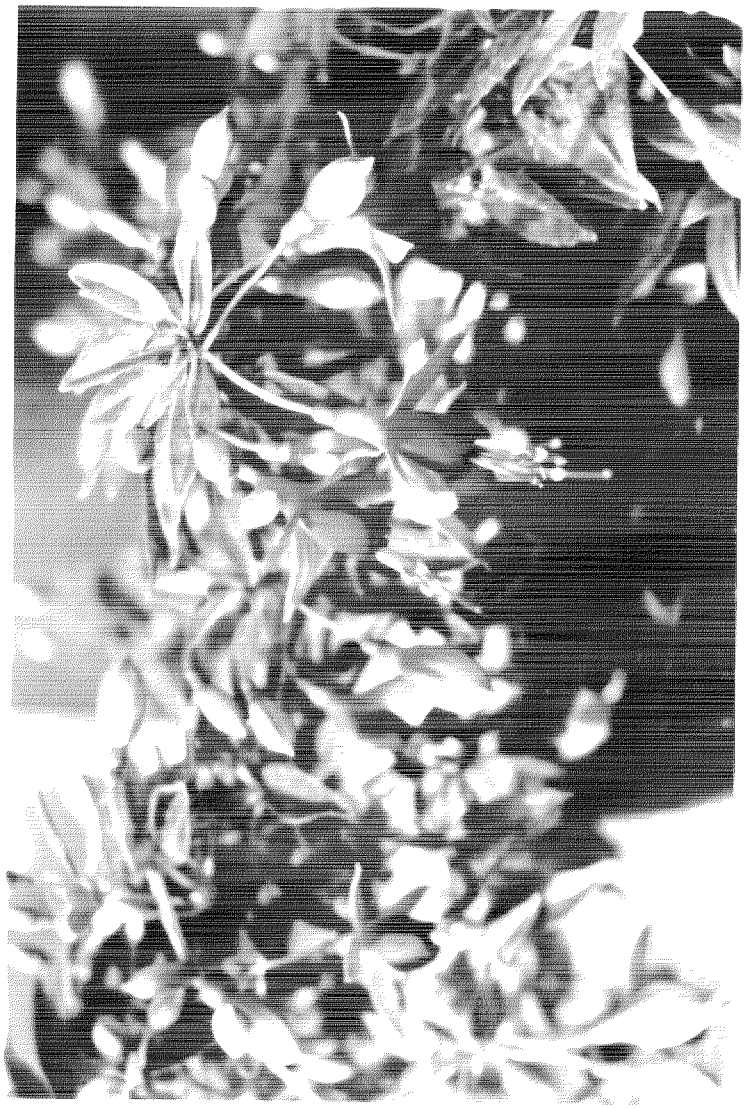
FIG. 2 is a photograph of flowers of the new variety of fuchsia plant.

The botanical characteristics of the new and distinct variety of fuchsia plant "Sanicomf" are as follows.

Plant:

*Growth habit.*—Spreading.
*Plant height.*—Low.
*Grade of bushiness.*—Many.

Stem:

*Thickness.* —2.1 mm.
*Color.*—Red.
*Pubescence.*—Absent.
*Branching.*—Many.
*Length of internode.*—Short.

Leaf:

*Phyllotaxis.*—Verticillate, partially opposite.
*Shape.*—Oblong.
*Tip form of leaf.*—Acute.
*Base form of leaf.*—Orbicular.
*Shape of Margin.*—Dentate serrate.
*Length.*—37.1 mm.
*Width.*—17.5 mm.
*Thickness.*—0.4 mm.
*Color of upper surface of new leaf.*—Grayish olive green. (R.H.S. 137A, JHS 3716).
*Color of upper surface of mature leaf.*—Grayish olive green. (R.H.S. 137A, JHS 3716).
*Color of under surface of mature leaf.*—Grayish yellow green. (R.H.S. 138B, JHS 3715).

*Variegation on upper surface.*—Absent.
*Color of leaf vein.*—Pale green.
*Luster.*—Absent.
*Pubescence of upper surface.*—Absent.
*Pubescence of under surface.*—Absent.
*Length of petiole.*—8.7 mm.
*Width of petiole.*—1.0 mm.
*Color of petiole.*—Moderate purplish red. (R.H.S. 64C, JHS 9512).
*Pubescence of petiole.*—Few.

Flower:
*Inflorescence types.*—Leaf axil—single.
*Facing direction.*—Slightly downward to horizontal.
*Type.*—Single.
*Diameter.*—40.5 mm.
*Length.*—26.9 mm.
*Diameter of corolla.*—Medium.
*Shape of petal.*—Obovate.
*Length of petal.*—15.9 mm.
*Width of petal.*—18.6 mm.
*Thickness of petal.*—0.4 mm.
*Number of petals.*—Medium; 4.
*Color of petal at the beginning of blooming time.*—Deep violet. (R.H.S. 93A, JHS 8006).
*Color of petal at blooming time.*—Deep violet. (R.H.S. 93A, JHS 8006).
*Variegated pattern of petal.*—Absent.
*Shape of sepal.*—Oblong.
*Tip form of sepal.*—Acuminate.
*Calyx rolling.*—Weak (horizontal).
*Intorsion of sepal.*—None.
*Curvature of sepal.*—Outcurve.
*Length of sepal.*—23.5 mm.
*Width of sepal.*—8.8 mm.
*Thickness of sepal.*—0.5 mm.
*Number of sepals.*—Medium; 4.
*Color of sepal.*—Deep purplish pink. (R.H.S. 55A, JH 9705).
*Variegated pattern on sepal.*—Absent.
*Shape of calyx tube.*—Long-tubular.
*Thickness of calyx tube.*—6.3 mm.
*Length of calyx tube.*—7.5 mm.
*Color of calyx tube.*—Deep purplish pink. (R.H.S. 55A, JHS 9705).
*Variegated pattern on calyx tube.*—Absent.
*Length of pistil.*—Long.
*Color of pistil.*—Vivid red. (R.H.S. 52A, JHS 0106).
*Color of stigma.*—Pale purplish pink. (R.H.S. 65C, JHS 9502).
*Length of stamen.*—Medium.
*Color of stamen.*—Deep purplish pink. (R.H.S. 55A, JHS 9705).
*Number of stamens.*—Medium; 8.
*Thickness of peduncle.*—Medium.
*Length of peduncle.*—Medium.
*Color of peduncle.*—Light yellow green. (R.H.S. 144D, JHS 3503).
*Shape of ovary.*—Oblong.
*Length of ovary.*—Medium.
*Color of ovary.*—Strong yellow green. (R.H.S. 144A, JHS 3507).
*Number of flowers.*—Medium.
*Flower fragrance.*—Absent.
*Floriferousness.*—Numerous.
*Grade of seed fertility.*—Medium.
*Grade of floral abscission.*—Medium.
*Blooming time.*—Early.
*Flowering duration.*—Long; early May to the middle of December.

Physiological and ecological characteristics:
*Grade of cold resistance.*—Strong.
*Grade of heat resistance.*—Strong.
*Grade of disease resistance.*—Strong.
*Grade of pest resistance.*—Strong.

This new variety of fuchsia plant is most suitable for flower potting, particularly in hanging pots.

The plant of this new variety "Sanicomf" is presently planted and maintained at the Plant Biotechnology Laboratory of Suntory Ltd., residing at 863-1, Aza-Iketani, Oomori-cho, Youkaichi-shi, Shiga ken, Japan and at the Plant Research Center of Nishinomiya-shi, residing at 1-1, Kitayama-cho, Nishinomiya-shi, Hyogo-ken, Japan.

We claim:

1. A new and distinct variety of fuchsia plant, substantially as herein illustrated and described, characterized particularly as to novelty by (A) having a spreading growth habit of strongly bushy form, low plant height, fine branching, and short internode length, (B) great profusion of blooms, the whole bush remaining in bloom for a considerable period of time, and very long flowering duration, (C) having flowers which are single without variegated pattern on petals which are deep violet color, (D) having deep purplish pink colored sepals without variegated pattern and deep purplish pink colored calyx without variegated pattern, and (E) a high resistance to heat, cold, disease and pests.

* * * * *